(12) United States Patent
Malkus et al.

(10) Patent No.: US 7,777,995 B2
(45) Date of Patent: Aug. 17, 2010

(54) POLE-MOUNTABLE MEDICAL EQUIPMENT POWER SUPPLY HAVING LOW PATIENT LEAKAGE CURRENT

(75) Inventors: Tim Malkus, Severn, MD (US); Kenneth M. Eshenbaugh, Gaithersburg, MD (US); Richard Stacey, Clarksville, MD (US); John O. Taylor, Annapolis, MD (US)

(73) Assignee: American IV, Inc., Harmans, MD (US)

( * ) Notice: Subject to any disclaimer, the term of this patent is extended or adjusted under 35 U.S.C. 154(b) by 313 days.

(21) Appl. No.: 11/838,001

(22) Filed: Aug. 13, 2007

(65) Prior Publication Data

US 2009/0046402 A1 Feb. 19, 2009

(51) Int. Cl.
*H02H 3/00* (2006.01)
*H02H 9/08* (2006.01)

(52) U.S. Cl. ........................................ 361/42
(58) Field of Classification Search .................... 361/42
See application file for complete search history.

(56) References Cited

U.S. PATENT DOCUMENTS

| | | | | |
|---|---|---|---|---|
| 3,225,155 A | * | 12/1965 | Duncan | 200/51.09 |
| 3,665,252 A | * | 5/1972 | Rogers et al. | 361/50 |
| 3,699,392 A | * | 10/1972 | Lee et al. | 361/49 |
| 6,594,146 B2 | * | 7/2003 | Frangesch et al. | 361/679.02 |
| 6,612,664 B2 | * | 9/2003 | Pryor et al. | 312/198 |
| 6,641,237 B1 | * | 11/2003 | Pryor et al. | 312/245 |
| 2002/0082479 A1 | * | 6/2002 | Frangesch et al. | 600/300 |
| 2002/0113529 A1 | * | 8/2002 | Pryor et al. | 312/221 |
| 2008/0116157 A1 | * | 5/2008 | Fulbrook et al. | 211/60.1 |

\* cited by examiner

*Primary Examiner*—Ronald W Leja
(74) *Attorney, Agent, or Firm*—Womble Carlyle Sandridge & Rice, PLLC

(57) ABSTRACT

A medical electrical equipment power supply is configured to satisfy at least one industry standard for patient leakage current. The power supply is provided with a plurality of electrical sockets into which IV pumps, patient monitors and other equipment may be plugged in. In one embodiment, the power supply has a housing configured to be mounted on an IV pole. An isolation transformer within the housing helps reduce the total patient leakage current to a value that satisfies at least one industry standard for patient leakage current. In another embodiment devoid of an isolation transformer, the power supply's electrical circuit detects whether the patient leakage current exceeds a predetermined value based on the industry standard, and disconnects power to one or more sockets so as to maintain the patient leakage current below this predetermined value.

25 Claims, 15 Drawing Sheets

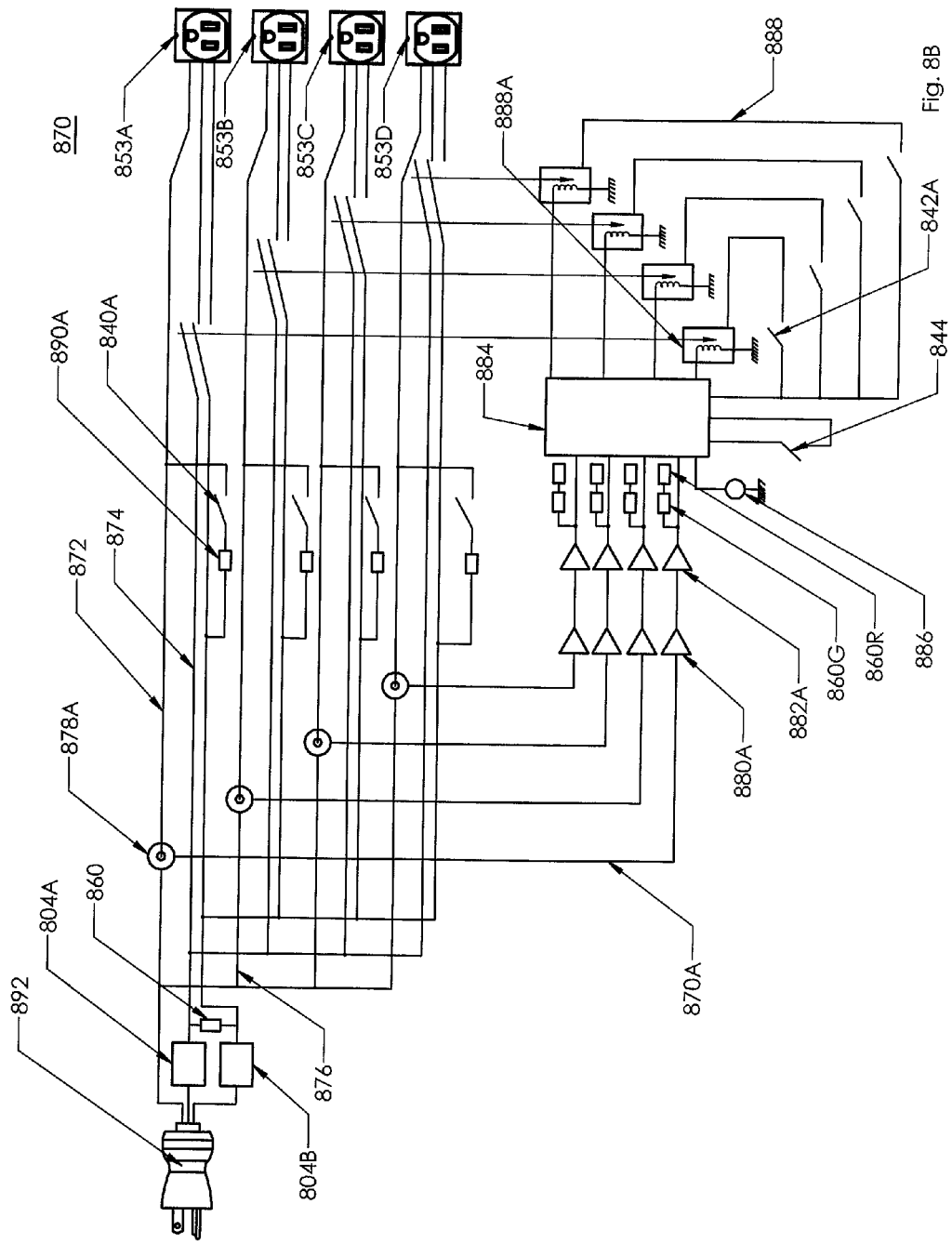

US 7,777,995 B2

POLE-MOUNTABLE MEDICAL EQUIPMENT POWER SUPPLY HAVING LOW PATIENT LEAKAGE CURRENT

BACKGROUND OF THE INVENTION

1. Field of the Invention

The present invention concerns a power supply which can be mounted on a pole, such as a pole for hanging intravenous fluids, and other equipment. More particularly, it concerns a power supply which controls total patient leakage current to the low levels required by one or more national or international standards applicable to this type of medical electrical equipment.

2. Background

There are many industry standards governing medical electrical equipment, such as IV pumps, patient monitors, and the like, that are used in medical and clinical settings. The international industry standard IEC 60601-1 requires that maximum patient touch current (the current flowing between the patient and ground) from all such devices does not exceed 100 µA (microamps). Underwriter's Laboratories has established standard UL 60601-1, which has similar requirements and serves as a de facto industry standard in the U.S. and Canada. Generally speaking, hospitals in the U.S. and Canada will not allow medical electrical equipment to be used unless they meet UL standards. A maximum patient touch current of 100 µA is difficult to achieve using normal power strips and one conventional solution is to have a large isolation transformer in a box sitting on the floor near the wall outlet. Various medical electrical equipment may then be plugged into this box. This achieves the requirement to control the patient touch current. However, the box is typically near the wall and running multiple cables from the various medical electrical equipment devices to the box is cumbersome. Furthermore, many cables that come with their respective devices are not sufficiently long to allow this, requiring extension cords, and further increasing the patient leakage current and creating potential trip hazards.

Oftentimes, such items of medical electrical equipment are mounted on an Intravenous (IV) pole, which typically is supported by wheeled legs, to facilitate positioning and transport. Current state-of-the art power supplies, such as the AIV POWERMATE™, marketed by American IV Products, Inc. dba AIV, Inc. of Harmans, Md., U.S.A., may be mounted on such an IV pole via a mounting assembly formed on the backside of the unit. The various medical electrical equipment mounted on the IV pole may then be plugged into this power supply. However, this would not meet the IEC 60601-1 patient leakage current industry standard.

SUMMARY OF THE INVENTION

In one aspect, the present invention is directed to a pole-mountable medical electrical equipment power supply that satisfies at least one industry standard for patient leakage current. This power supply includes a housing adapted to be mounted on a pole and a plurality of electrical sockets suitable for receiving plugs, provided on the housing. The power supply comprises a first type of electrical circuit. The first type of electrical circuit comprises an isolation transformer supported by the housing, the isolation transformer connecting power from an electrical outlet to the electrical sockets, when said power supply is plugged into an electrical outlet.

In another aspect, the present invention is directed to a medical electrical equipment power supply that satisfies at least one industry standard for patient leakage current. This power supply includes a housing having a plurality of electrical sockets suitable for receiving plugs provided thereon. The power supply comprises a second type of electrical circuit. The second type of electrical circuit comprises: at least one current sensor configured to measure a patient leakage current, when the power supply is plugged into an electrical outlet and is used to power at least one item of medical electrical equipment connected to a patient; a detection circuit configured to determine whether the patient leakage current measured by the at least one current sensor exceeds a predetermined value based on said industry standard, and output at least one control signal in response thereto; and a power control circuit configured to disconnect power to at least one of said electrical sockets in response to said at least one control signal, so that the at least one industry standard for patient leakage current remains satisfied. The housing may be adapted to be mounted on a pole.

In yet another aspect, the present invention is directed to an IV pole in combination with a pole-mountable medical electrical equipment power supply removably mounted to a pole member of the IV pole. The power supply satisfies at least one industry standard for patient leakage current. At least two items of medical electrical equipment are plugged into the power supply.

In one embodiment, the power supply has the first type of electrical circuit. In another embodiment, the power supply has the second type of electrical circuit.

In still another aspect, the present invention is directed to an IV pole in combination with a medical electrical equipment power supply non-removably fixed thereto, wherein said medical electrical equipment power supply comprises: a housing and a plurality of electrical sockets suitable for receiving plugs provided on the housing; and electrical circuitry configured such that the power supply satisfies at least one industry standard for patient leakage current.

In one embodiment, the power supply has the first type of electrical circuit. In another embodiment, the power supply has the second type of electrical circuit.

BRIEF DESCRIPTION OF THE DRAWINGS

FIG. 8B shows a circuit diagram for the power supply of FIG. 8A.

DETAILED DESCRIPTION OF THE INVENTION

Figure 1:
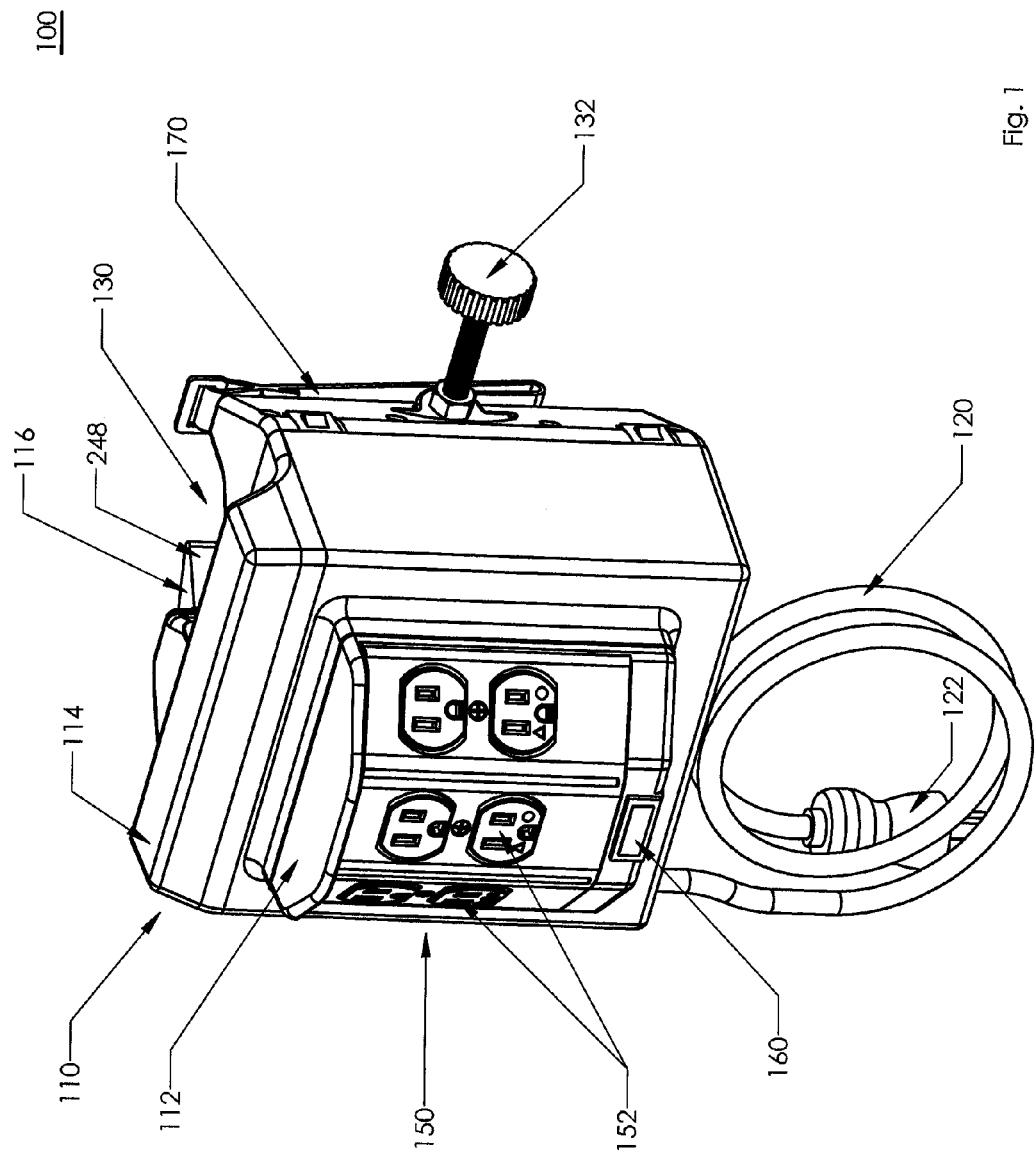
FIG. 1 shows a front perspective view of one embodiment of a power supply in accordance with the present invention.
Figure 1A:
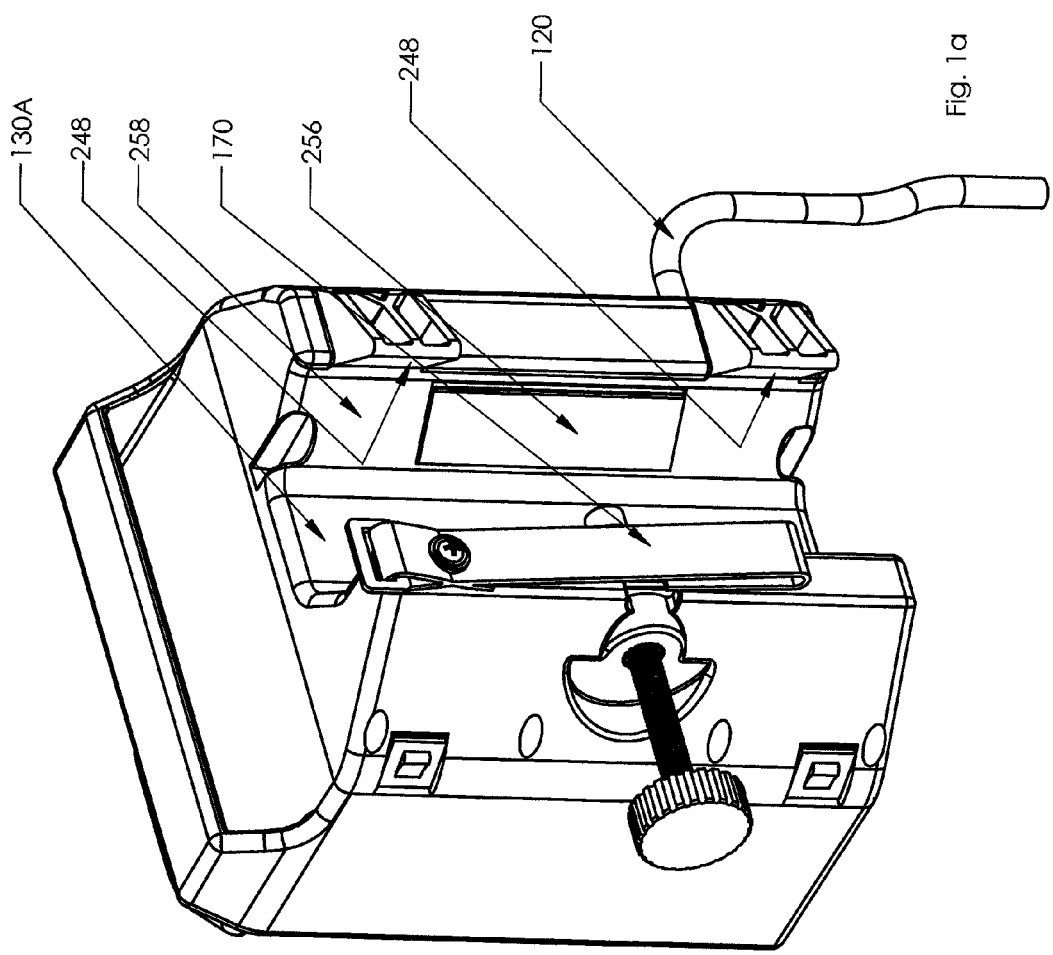
FIG. 1A shows a rear perspective view of the power supply of FIG. 1.

The international industry standard, IEC 60601-1 is incorporated by reference to the extent necessary to understand the present invention. It is understood that this industry standard may change from time to time. One aspect of this industry standard that is particularly relevant to the present invention is that the patient leakage current, from all medical electrical equipment, be below a predetermined value. Currently, per the industry standard, this value is 100 μA.

FIGS. 1, 1A, 2, 3 and 3A show one embodiment of a power supply 100 in accordance with the present invention. The power supply 100 includes a housing 110 which, in the embodiment shown, includes a front housing 112, a middle housing 114 and a rear housing 116. The front housing 112 supports a socket cluster 150 comprising a plurality of dual receptacles 152, each comprising a pair of sockets 153 suitable for receiving plugs from medical electrical equipment. In a preferred embodiment, the dual receptacles 152 are hospital grade receptacles. A power-on indicator light 160 is provided on the front panel 112 to indicate when the power supply is plugged into an electrical socket.

A power cord 120 having a plug 122 enters the housing 100 via the rear housing 116, and supplies power from an electrical outlet to the isolation transformer 210 (described below), when the power supply 100 is plugged in. In one embodiment, the power cord is 16 AWG and between 10-20 feet long.

The rear housing 116 is provided with a longitudinal mounting assembly 130 suitable for mounting the power supply 100 to a pole. Within the meaning of the present invention, a "pole" is a structural member having a longitudinal extent, and a cross-section, such as the circular cross-section of a pole member of an IV pole, the square cross-section of a leg of a cart or hospital bed. Poles may also have other cross-sectional shapes, such as rectangular and triangular, among others. In the present invention, the term "pole-mountable" is intended to cover mounting assemblies that can be removably attached to poles of a variety of cross-sections. The mounting assembly 130 comprises a channel 130A into which such a pole is at least partially received. In one embodiment, the clamping assembly 130 is configured to be able to mount the power supply to a pole having a thickness, such as a diameter, of up to 2.5 inches, or roughly 6.5 cm.

A clamping screw 132 is provided to secure the power supply 100 to a pole, in cooperation with a pair of spaced apartment clamping surfaces 248 formed on the rear housing 116. The clamping screw 132 has a threaded shaft 232A terminating in an abutment cap 232B. The clamping screw passes through a clamping screw aperture 236 formed in a first exterior wall 238 of the rear housing 116, and is prevented from being completely withdrawn by an anti-removal locking nut 242 having a central hole too small for the abutment cap 232B to pass through. The clamping screw 132 extends in a first direction transverse to the channel 130A. The abutment cap 232B is capable of abutting a pole from one side. Meanwhile, the spaced apart clamping surfaces 248, which face in a second direction opposite the first direction, are capable of abutting a pole from the opposite side, when the power supply is positioned such that a portion of a pole is received into the channel. Thus, the clamping screw 132 and the pair of clamping surfaces 248 are capable of frictionally mounting the housing to a pole, when the power supply 100 is positioned such that a portion of a pole is received into the channel 130A. One or more friction-enhancing pads 256 may be provided on a wall 258 of the channel 130A to retard slippage of the power supply relative to the pole.

Figure 2:
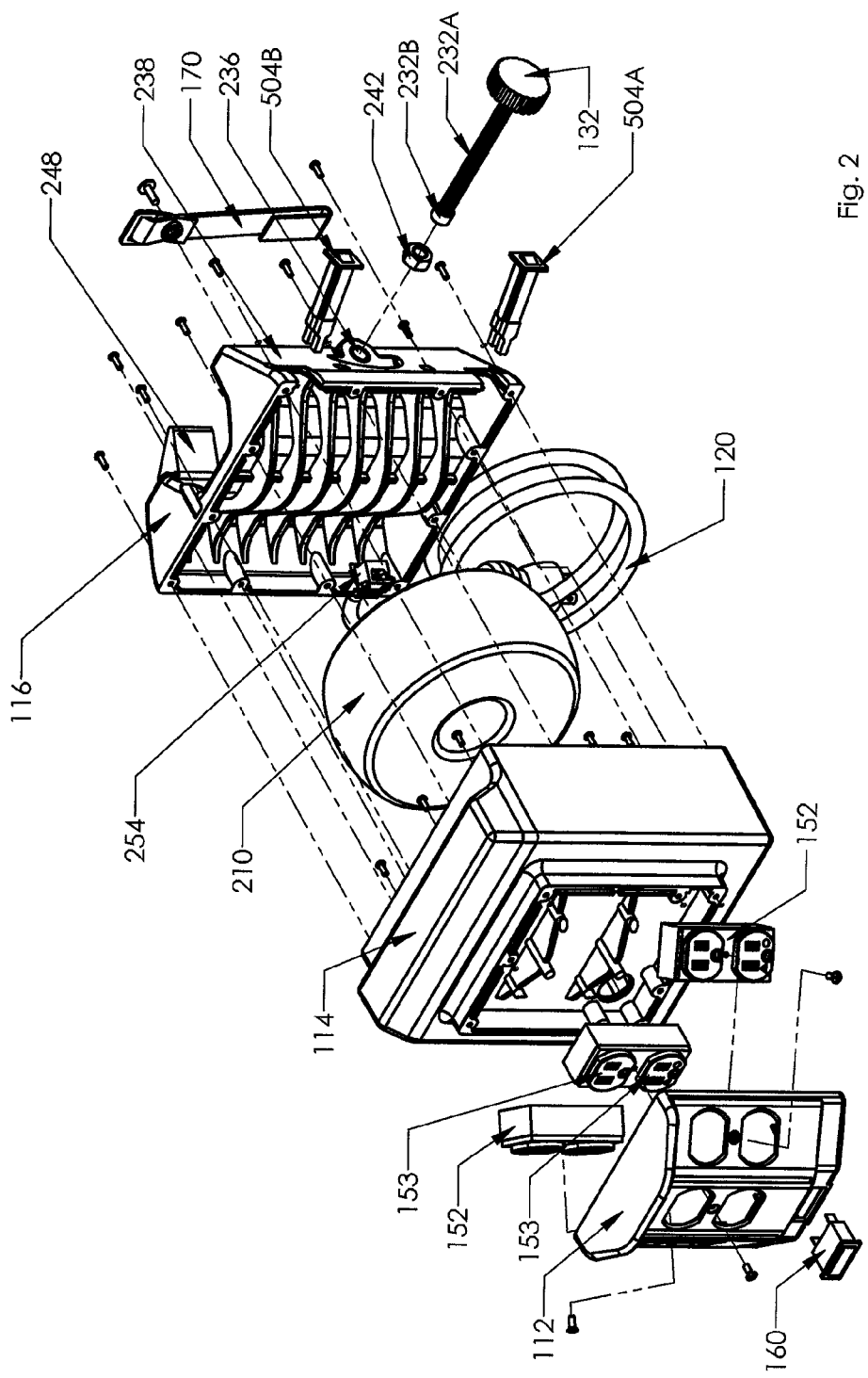
FIG. 2 shows an exploded view of the power supply of FIG. 1.

As seen in the exploded view of FIG. 2, in one embodiment, the isolation transformer 210 has a generally toroidal shape. It is understood, however, that the transformer 210 may take on other shapes as well, such as a cubic or paralellpiped shape. It is further understood that, in such case, the housing 110 may need to be altered to accommodate a different shape.

Figure 3:
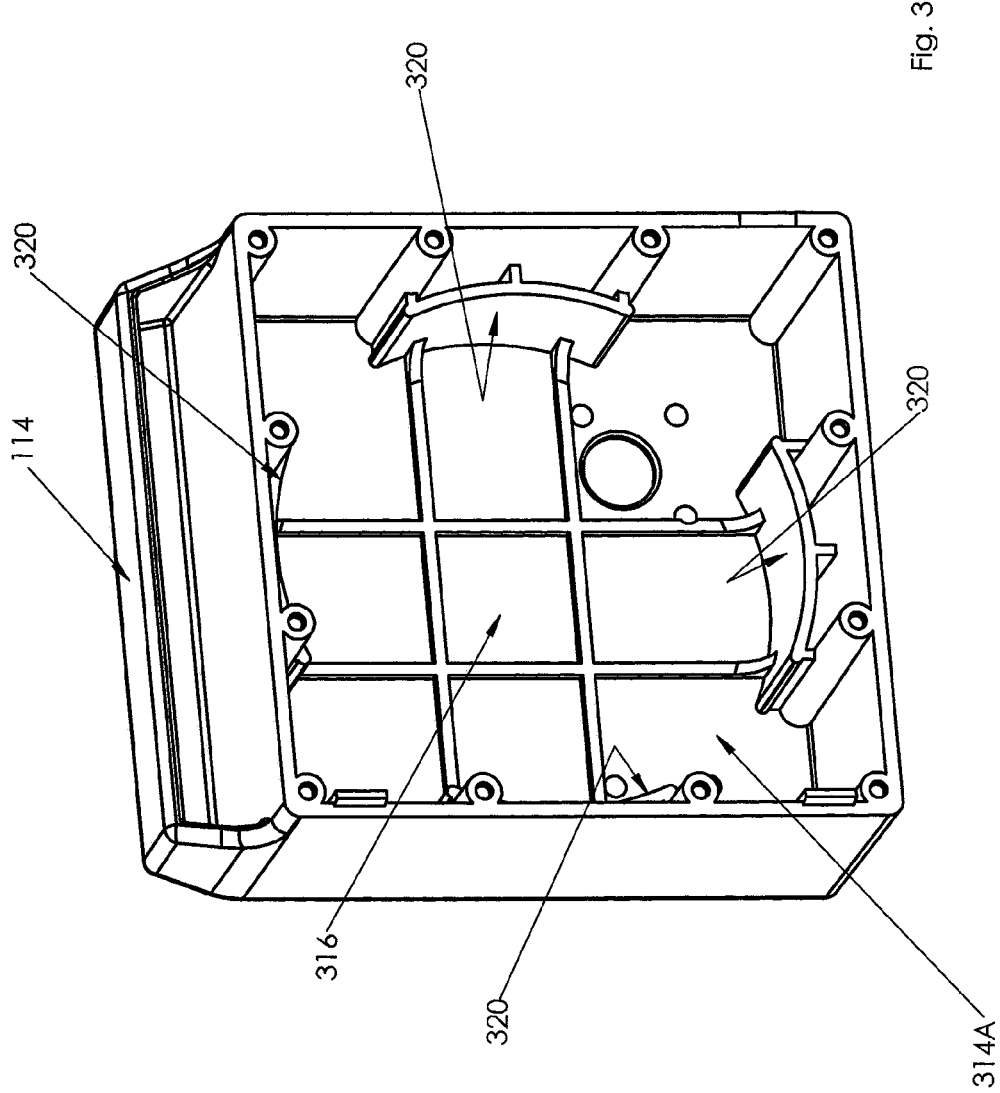
FIG. 3 shows a back view of the middle housing
Figure 3A:
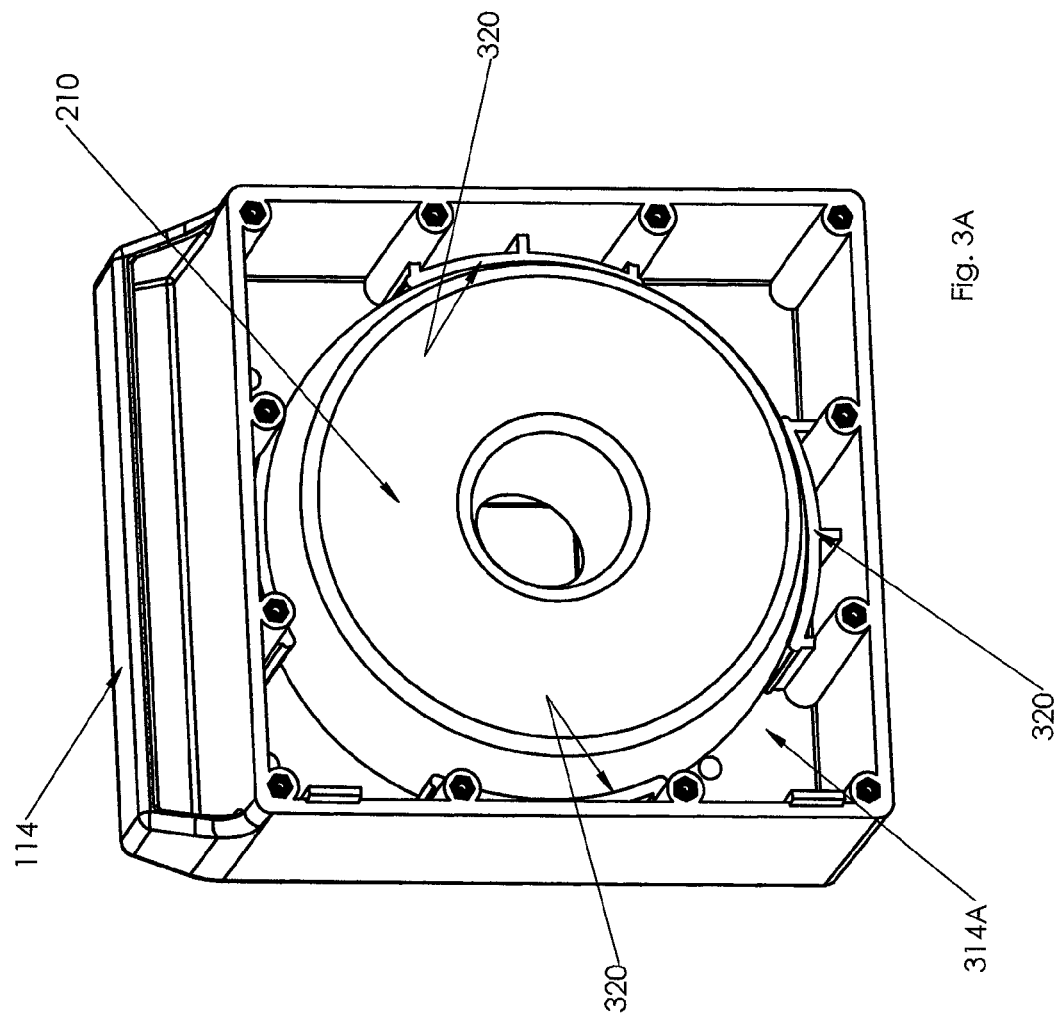
FIG. 3A shows a back view of the middle housing with the transformer mounted therein.

FIG. 3 shows a rear view of the middle housing 114. The rear side 314a of the middle housing has a cavity 316 configured and dimensioned to receive the isolation transformer 210. The cavity 316 is defined in part by a plurality of spaced apart projecting flanges 320 molded into the middle housing 114. In one embodiment, to accommodate a generally toroidal isolation transformer, each of the projecting flanges 320 has an arcuate cross-section with a radius approximately that of the isolation transformer, thereby defining a cylindrical cavity 316. As seen in FIG. 3A, isolation transformer 210 is received into the cylindrical cavity 316 formed on back side 314a of the middle housing 114, and snugly fits between the plurality of arcuate, spaced apart projecting flanges 320.

In one embodiment, the isolation transformer 210 has the following performance specifications: 120 Volt, 60 Hz, maximum output current of at least 6.0 Amps, a maximum leakage current of 100 μA, and a maximum temperature rise of 50° C. at full load. As to physical characteristics, the isolation transformer 210 has an outer diameter of about 6.4 inches, a thickness of about 2.5, and a weight of about 12 lbs.

Figure 5:
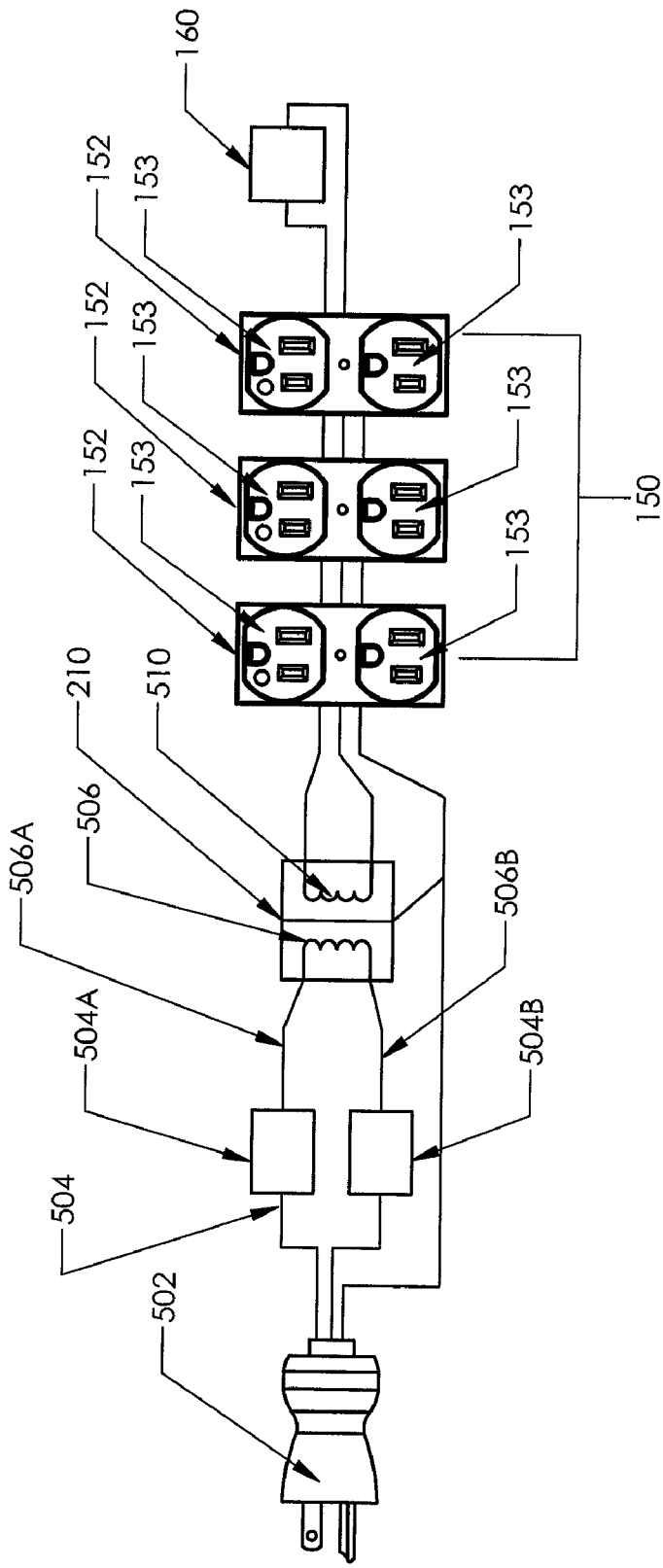
FIG. 5 shows an embodiment of an electrical circuit of the power supply of FIG. 1.

As seen in FIG. 5, the isolation transformer 210 belongs to an electrical circuit 500 that delivers power from an outlet to the receptacles 152. The electrical circuit 500 includes a plug 502 for inserting into a wall outlet or the like. A pair of circuit breakers 504A, 504B is in series with the plug 502 and with the arms 506A, 506B of the primary winding 506 of the isolation transformer 210. The circuit breakers 504A, 504B are configured to protect the power supply 100 from a power surge. The secondary winding 510 of the isolation transformer 210 is connected in series with the plurality of dual receptacles 152, thereby supplying power thereto. The indicator light 160 is also connected on this side of the isolation transformer 210 to indicate when the power supply is plugged in.

Figure 4:
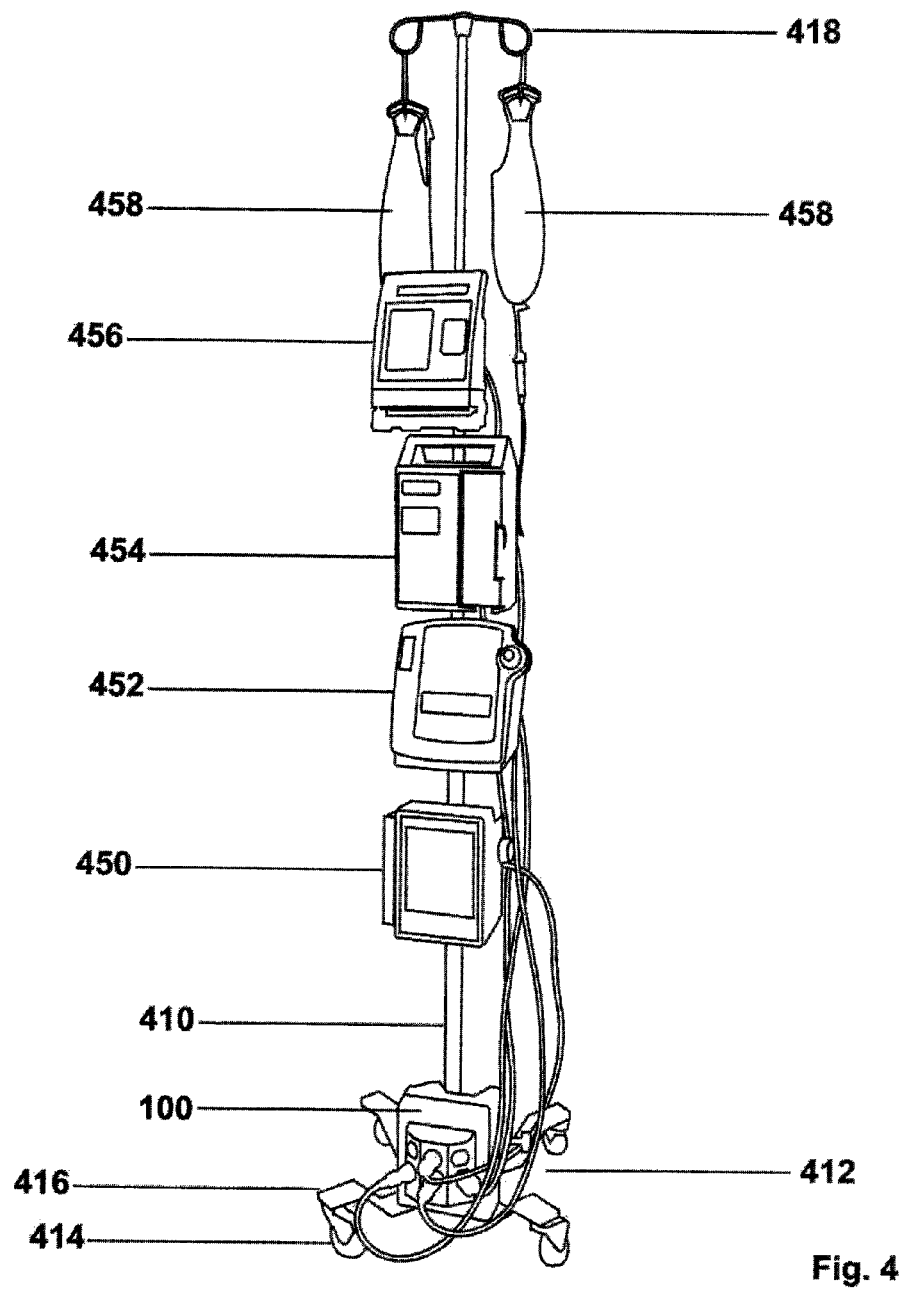
FIG. 4 shows the power supply of FIG. 1 in one embodiment of its environment.
Figure 4A:
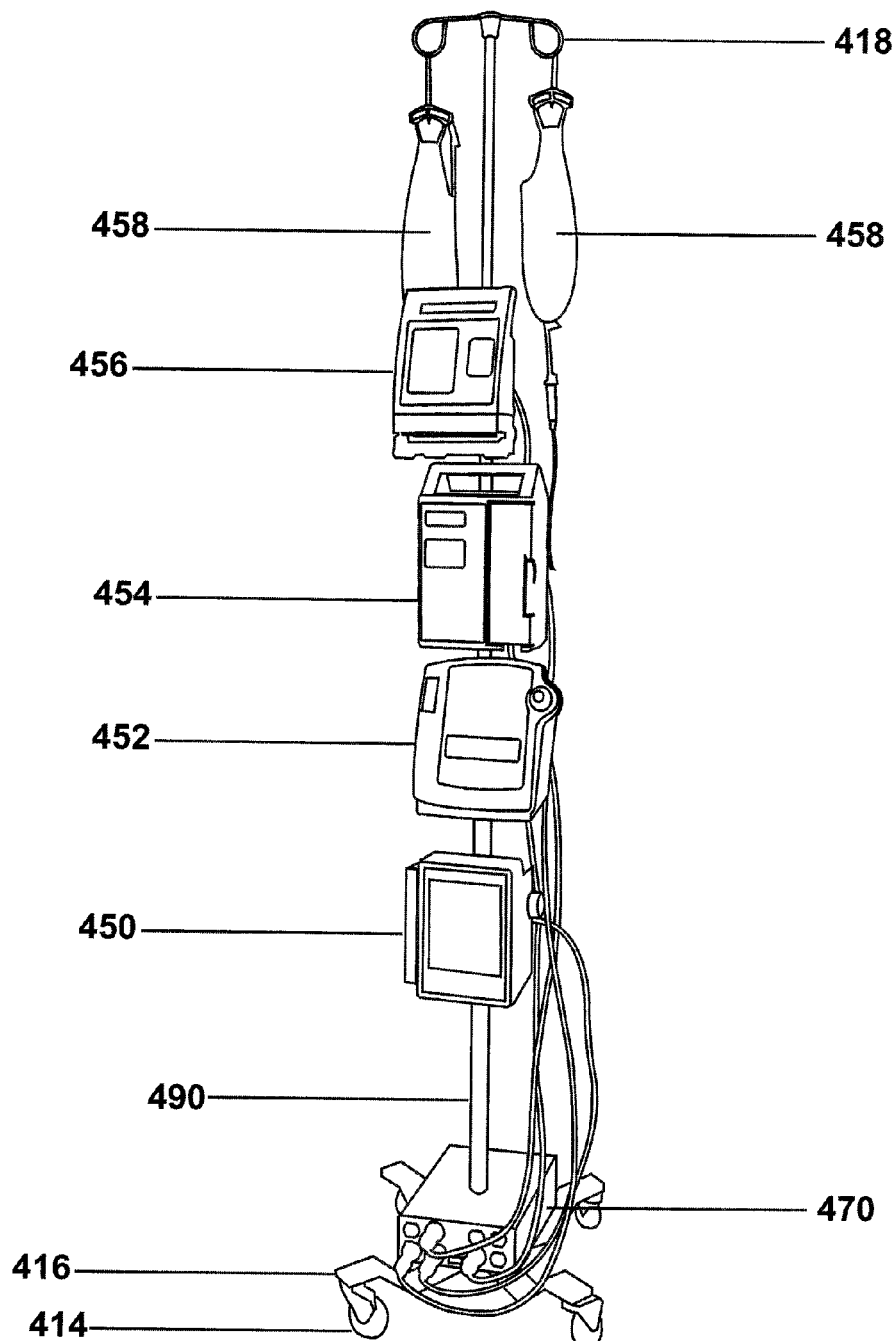
FIG. 4A shows an IV pole having a power supply non-removably fixed thereto by being built into the base of the IV pole.

FIG. 4 shows the power supply 100 being used in conjunction with an IV pole 400. The IV pole 400 comprises a base 412, a longitudinally extending pole member 410 and terminates at the top end in one or more hooks 418 for suspending IV bags. The base has a plurality of legs 416 provided with casters 414, to facilitate transport of the IV pole 400. The power supply 100 is mounted on the longitudinally extending pole member 410, proximate the base 412 of the IV pole 400. Mounting the power supply 100 close to base 412 lowers the center of gravity of the IV pole 400, thus reducing the likelihood of tipping during transport or other use.

As also seen in FIG. 4, assorted medical electrical equipment may be mounted on the longitudinally extending pole member 410 and plugged into the power supply. Thus, medical electrical equipment such as a breathing monitor 450, a blood pressure monitor 452, a heart monitor 454 and an IV pump 456, may be accommodated, along with one or more IV bags 458 may be suspended from the hooks 418. Each piece of equipment 450, 452, 5454, 456 may be connected to a single patient, and is plugged into the power supply 100.

The total patient leakage current from all these medical electrical devices must meet any applicable patient leakage current industry standard, such as the pertinent industry standard set forth by IEC 60601-1, and/or UL 60601-1. Currently, the applicable patient leakage current industry standard in IEC 60601-1 is a total patient leakage of less than 100 μA. Thus, the industry standard may be satisfied with the power supply 100 in accordance with the present invention.

FIGS. 6A-8C show a second embodiment of a power supply 600, 700, 800 in accordance with the present invention.

Figure 6A:
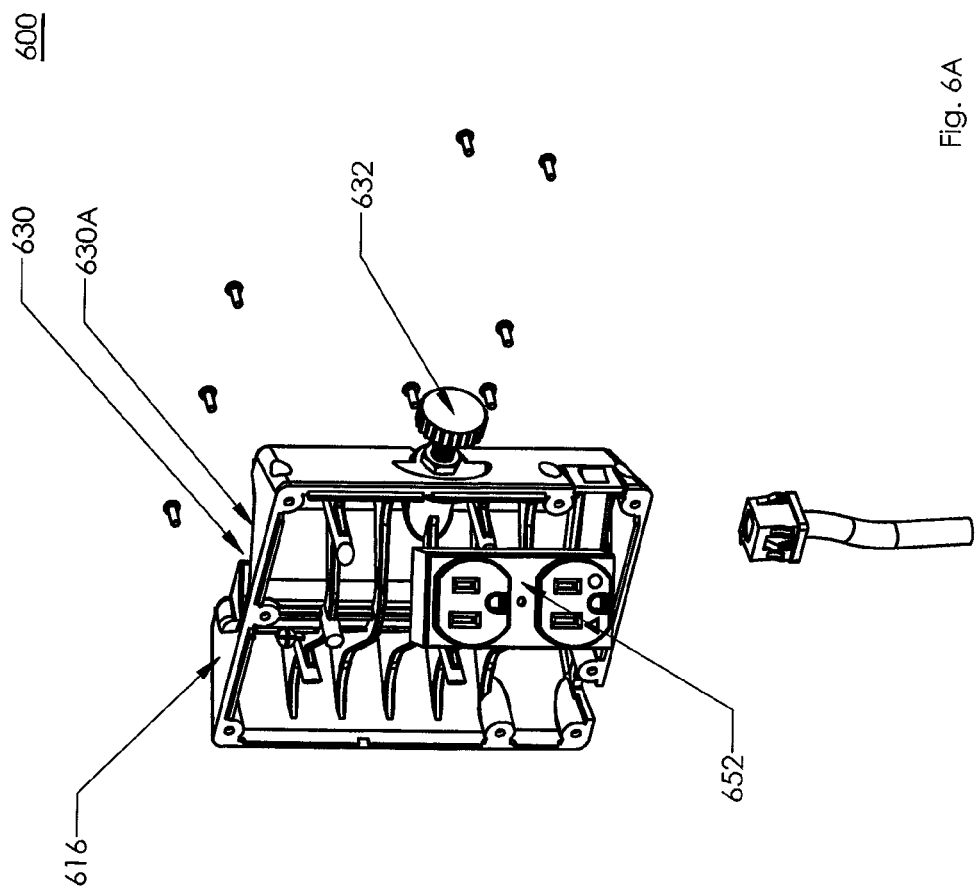
FIG. 6A shows an exploded view of a power supply of a first type in accordance with a second embodiment of the present invention.
Figure 6A:
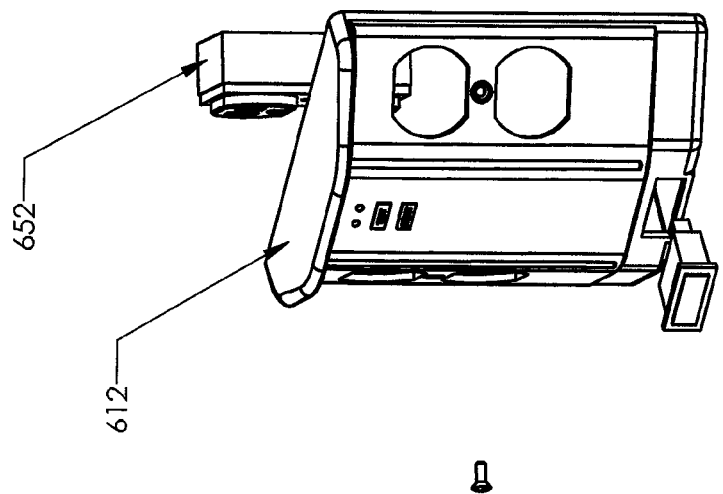
Figure 6B:
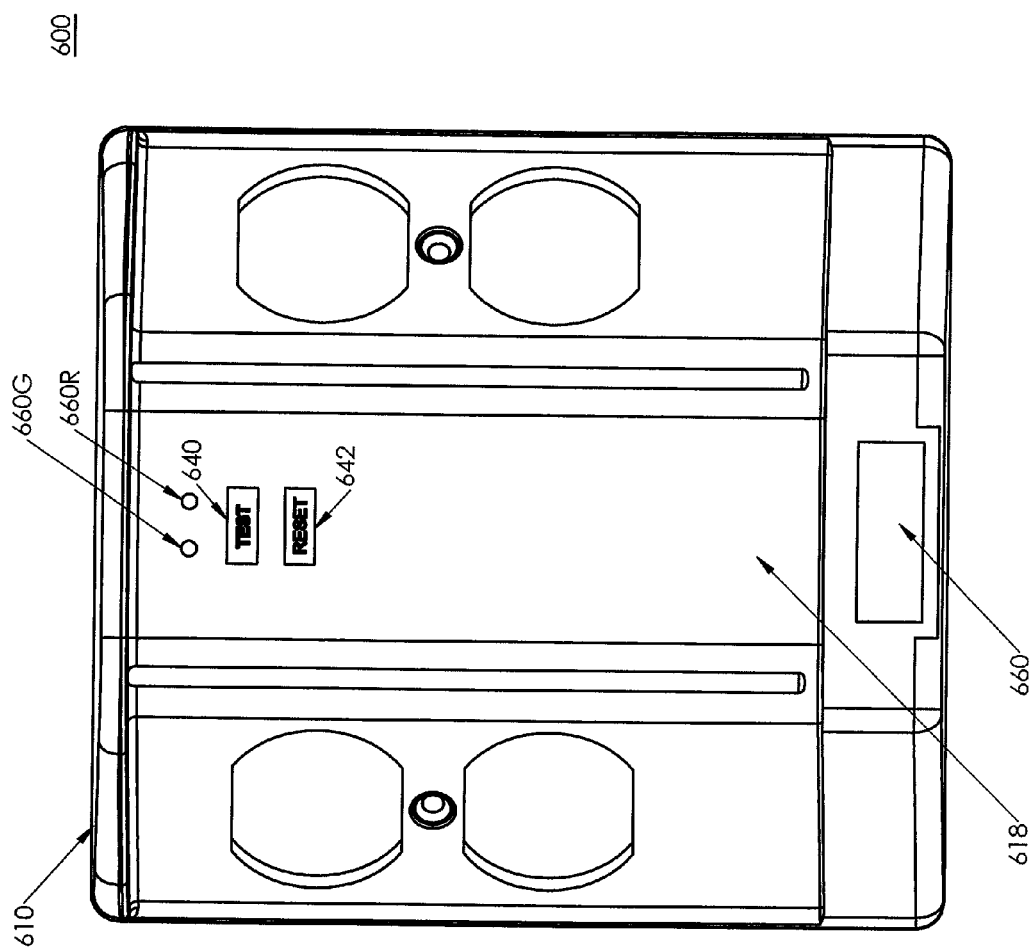
FIG. 6B shows a front view of the power supply of FIG. 6A.
Figure 6C:
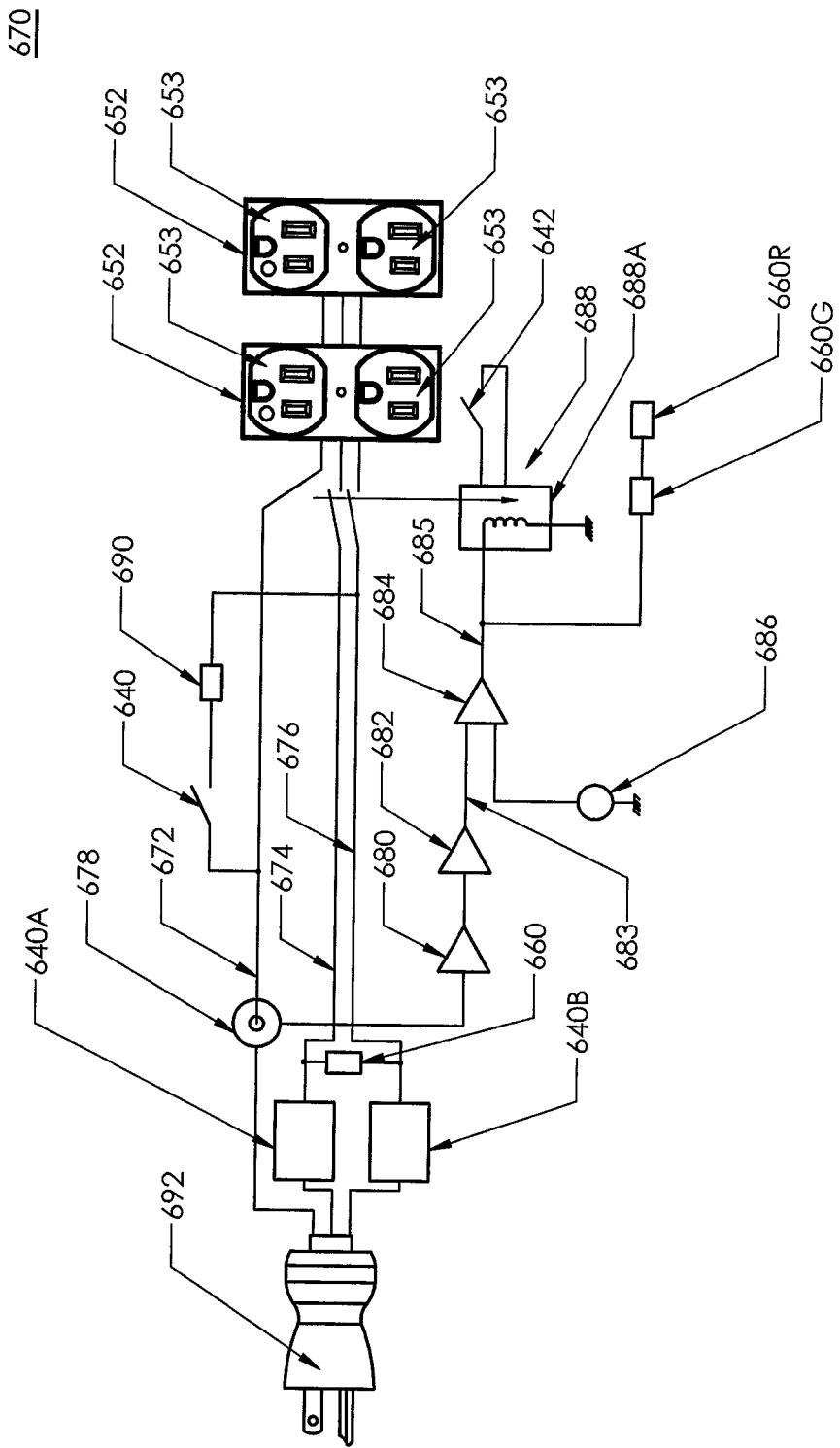
FIG. 6C shows a circuit diagram for the power supply of FIG. 6.

FIGS. 6A-6C show a first type of power supply 600 in accordance with the second embodiment of the present invention. The power supply 600 includes a housing 610 comprising a front housing 612 which connects to a rear housing 616. The front housing 612 supports a socket cluster comprising a plurality (two, in this embodiment) of hospital-grade dual receptacles 652, each receptacle comprising two sockets. The sockets 653 of the dual receptacles 652 are suitable for receiving plugs from medical electrical equipment. It is understood once again that the dual receptacles 652 are hospital grade receptacles. The back side of the rear housing 616 is provided with a longitudinal mounting assembly 630 including channel 630A and a clamping screw 632, much the same as found in the power supply 100 of the first embodiment, and so is also pole-mountable.

As seen in FIG. 6B, the front face 618 of the front housing 612 is provided with a power-on indicator light 660, a single test button 640 and a single reset button 642. Also visible on the front housing are a green indicator light 660G signifying that the unit is working all right and that the patient leakage current is below a predetermined threshold, and a red indicator light 660R signifying a fault condition, such as the patient leakage current exceeding a predetermined threshold. In one embodiment, so long as the power supply 600 is plugged into to line current, exactly one of the green indicator light 660G and the red indicator light 660R will be on, at any given time.

FIG. 6C shows an electrical circuit 670 corresponding to the first variation of the second embodiment. A plug 692 is connected to ground 672, neutral 674 and line 676 leads. A pair of circuit breakers 604A, 604B are provided on two of the leads. A current sensor 678 connects to the ground lead 672 to sense the patient leakage current. The current sensor 678 comprises circuitry including a transformer which converts the sensed leakage current to a leakage voltage, thus allowing for the non-invasive measurement of the leakage current.

The output of the current sensor 678, in the form of a leakage voltage, is passed though a 60 Hz bandpass filter 680 and then to an amplifier 682. The amplifier output 683 is thus reflective of the patient leakage current on the ground lead 672. The amplifier output 683 is then applied to a detection circuit 684. A predetermined reference voltage 686 is also applied to the detection circuit 684. The predetermined reference voltage 686 corresponds to a patient leakage current on the ground lead 672 exceeding some predetermined threshold. The predetermined threshold is a value based on an industry standard, after allowing for a margin of safety. For instance, if the industry standard calls for a maximum total patient leakage current of 100 μA, and one wishes a safety margin of 10 μA, then the predetermined reference voltage would correspond to patient leakage current (on the ground lead 672) of 90 μA.

In one embodiment, the detection circuit 684 comprises a comparator. In another embodiment, the detection circuit 684 comprises a processor. Regardless of how the detection circuit 684 is implemented, it compares the amplifier output 683 with this predetermined reference voltage 686, and outputs at least one control signal 685.

The control signal 685, which typically occupies one of two values, is then used to control a power control circuit 688 and drive an indicator light 660. In one embodiment, the power control circuit comprises a relay 688A, which may be a double pole relay which selectively connects or disconnects the neutral lead 674 and the line lead 676 to/from the receptacles 652. When the control signal 685 is at a first level, the relay 688A connects both leads 674, 676 to the receptacles 652. This is the normal operating condition. However, when the control signal 685 is at a second level, such as when the patient leakage current exceeds the predetermined threshold, the relay 688A is triggered by the control signal 685 and the leads 674, 676 are disconnected from the receptacles 652. If the receptacles have been disconnected, then the red indicator light 660R turns on (and the green indicator light 660G turns off) to serve as a visible indicator that power to the receptacles 652 has been disconnected. The control signal 685 may also be used to activate an audible indicator, such as a loudspeaker, to provide additional warning.

Figure 7A:
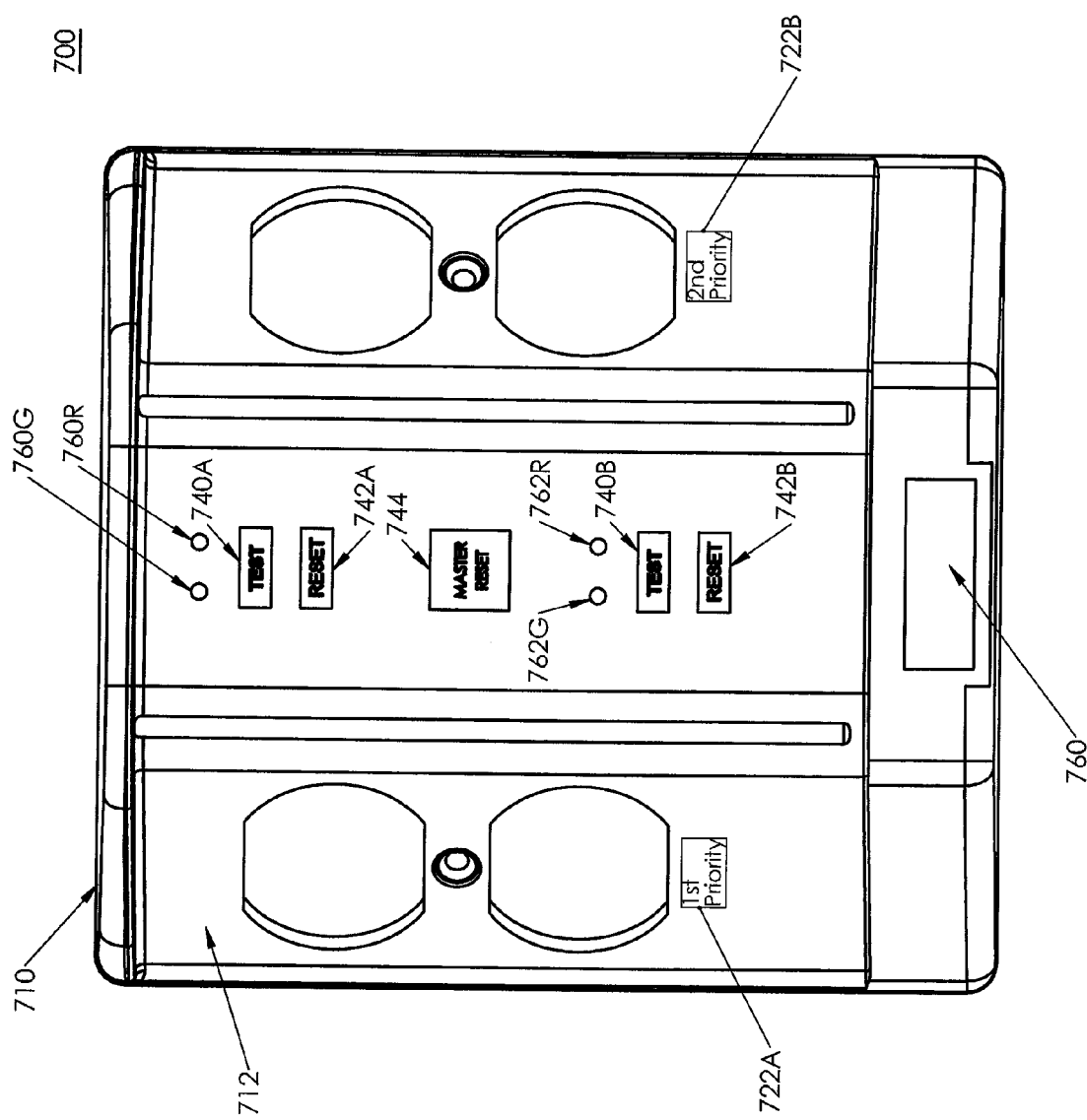
FIG. 7A shows a front view of a power supply of a second type in accordance with the second embodiment of the present invention.
Figure 7B:
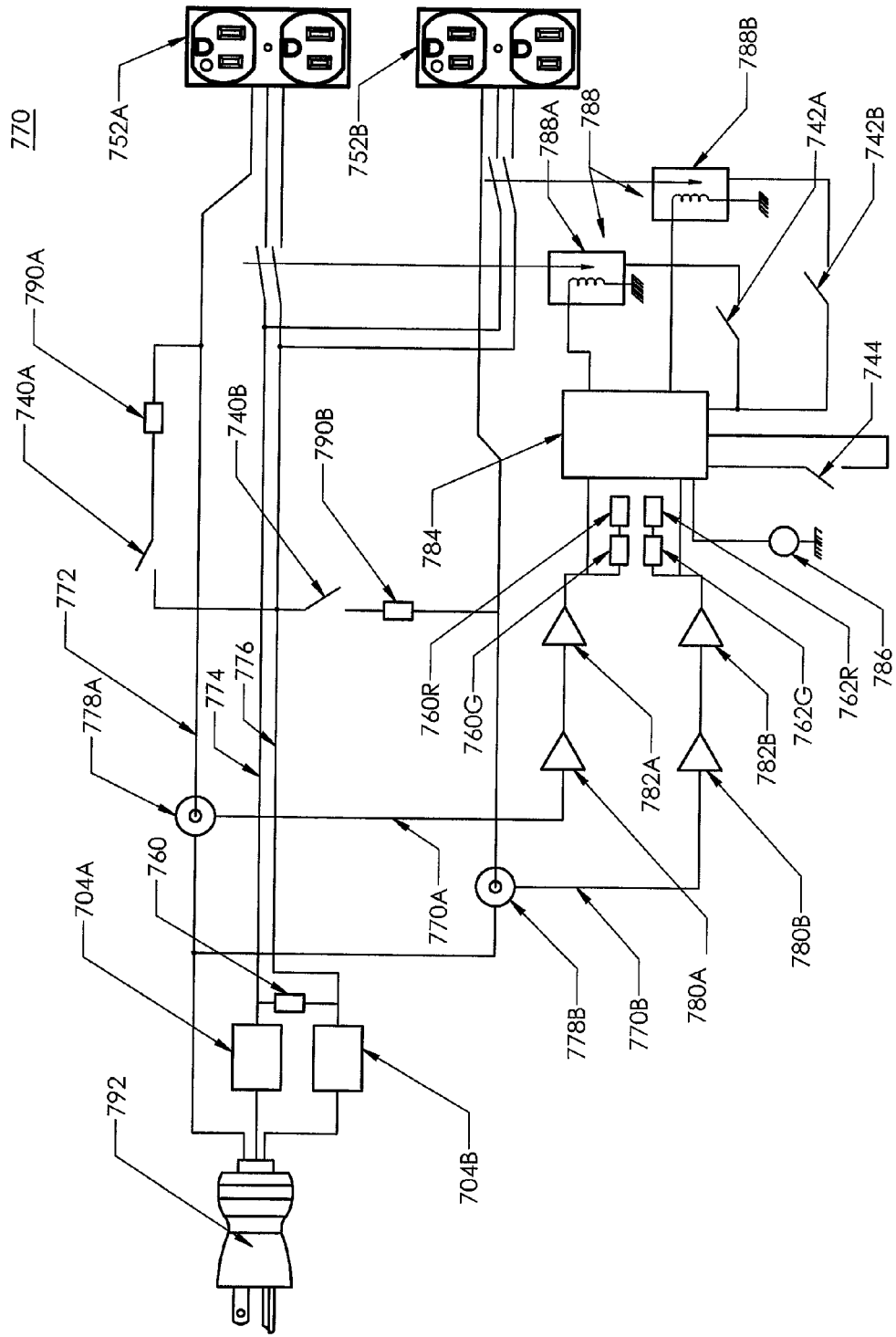
FIG. 7B shows a circuit diagram for the power supply of FIG. 7A.

The momentary contact test button 640 can be used to check whether the relay 688A is working properly. When the relay is set in the normal operating condition and the test button 640 is pushed, current temporarily flows from the line lead 676 through a current limiting resistor 690 to the ground lead 678. This current is sensed by the current sensor 678 and ultimately triggers the relay 688A, thereby disconnecting the leads 674, 676 from the receptacles 652. The reset button 642 is used to reset the relay 688A after neutral lead 674 and the line lead 676 are disconnected from the receptacles 652. Thus, the reset button 642 may be used either after the test button 640 has been pushed or after detection of an excessive patient leakage current triggers the relay 688A FIGS. 7A-7B show a second type of power supply 700 in accordance with the second embodiment of the present invention. Overall, the housing 710 of the power supply 700 is similar to the housing 610 of power supply 600. Though the front housing 712 has a power-on indicator light 760 much like power-on indicator light 660 in front housing 612, the front housing 712 differs somewhat from front housing 612 as described below.

As seen in FIG. 7B, the circuit 770 of power supply 700 includes a plug 792 connected to ground 772, neutral 774 and line 776 leads. A pair of circuit breakers 704A, 704B are provided on two of the leads. This is similar to circuit 660 of power supply 600. However, in contrast to circuit 670, circuit 770 comprises two parallel sub-circuits 770A, 770B, one for each hospital-grade dual receptacle 752A, 752B. Each of the sub-circuits 770A, 770B has its own test button 740A, 740B connected to a resistor 790A, 790B, and its own reset button 742A, 742B for resetting its power control circuit 788 (implemented again as a relay 788A, 788B). A master reset button 744 is provided to reset both dual receptacles 752A, 752B. On the sensing side, each sub-circuit 770A, 770B comprises a current sensor 778A, 778B, a 60 Hz bandpass filter 780A, 780B, an amplifier 782A, 782B, and indicator lights 760G, 760R, 762G, 762R, much the same as electrical circuit 670.

The detection circuit 784 in this embodiment comprises a processor. The processor 784 is configured to receive the amplified component voltage signals from the amplifiers 782A, 782B and sum them. Each component voltage signal is thus derived from one of the current sensors 778A, 778B. This results in a summed voltage that is proportional to the total patient leakage current experienced by the ground line 772. The processor 784 then compares this summed voltage with a reference voltage. While the reference voltage may comprise a voltage 786 that is input to the processor 784, it may instead simply be a value stored in memory associated with the processor.

If the comparison shows that the summed voltage exceeds the reference voltage, then the processor 784 is configured to decide which of the two receptacles 752A or 752B should be turned off, based on one more predetermined criteria.

In one embodiment, the power supply 700 may be configured such that one of the two dual receptacles 752A, 752B gets priority over the other. The priority of each dual receptacle may be indicated on the front housing 712 by means of indicia 722A, 722B such as numerals and/or words. This allows a user of the power supply 700 to plug the highest priority medical electrical equipment into sockets belonging to the dual receptacle that will most likely continue to receive power, even if the total patient leakage current from all such medical electrical equipment exceeds the industry standard.

Thus, if priority is given to dual receptacle 752A and the summed voltage from amplifiers 782A, 782B exceeds the reference voltage, the processor uses the individual component voltages received from the amplifiers 782A, 782B to determine whether the component voltage from amplifier 782A, by itself, is below the reference voltage. If so, the processor 784 then sends a signal to relay 788B to thereby disconnect power to dual receptacle 752B. If not, the processor 784 determines whether the component voltage from amplifier 782B, by itself, is below the reference voltage. If so, the processor 784 then sends a signal to relay 788A to thereby disconnect power to dual receptacle 752A. If, for some reason, the individual component voltages received from both amplifiers 782A, 782B exceed the reference voltage, then the processor 784 sends signals to both relays 788A, 788B, thereby disconnecting power to both dual receptacles 752A, 752B.

If power to a dual receptacle 752A, 752B has been disconnected, that dual receptacle's red error light 760R, 762R turns on. This serves as a visible indicator that devices plugged into that receptacle are not being powered by the power supply 700. The processor 784 may, in addition, output a signal to an audible indicator, such as a loudspeaker to serve as an additional warning.

Figure 8A:
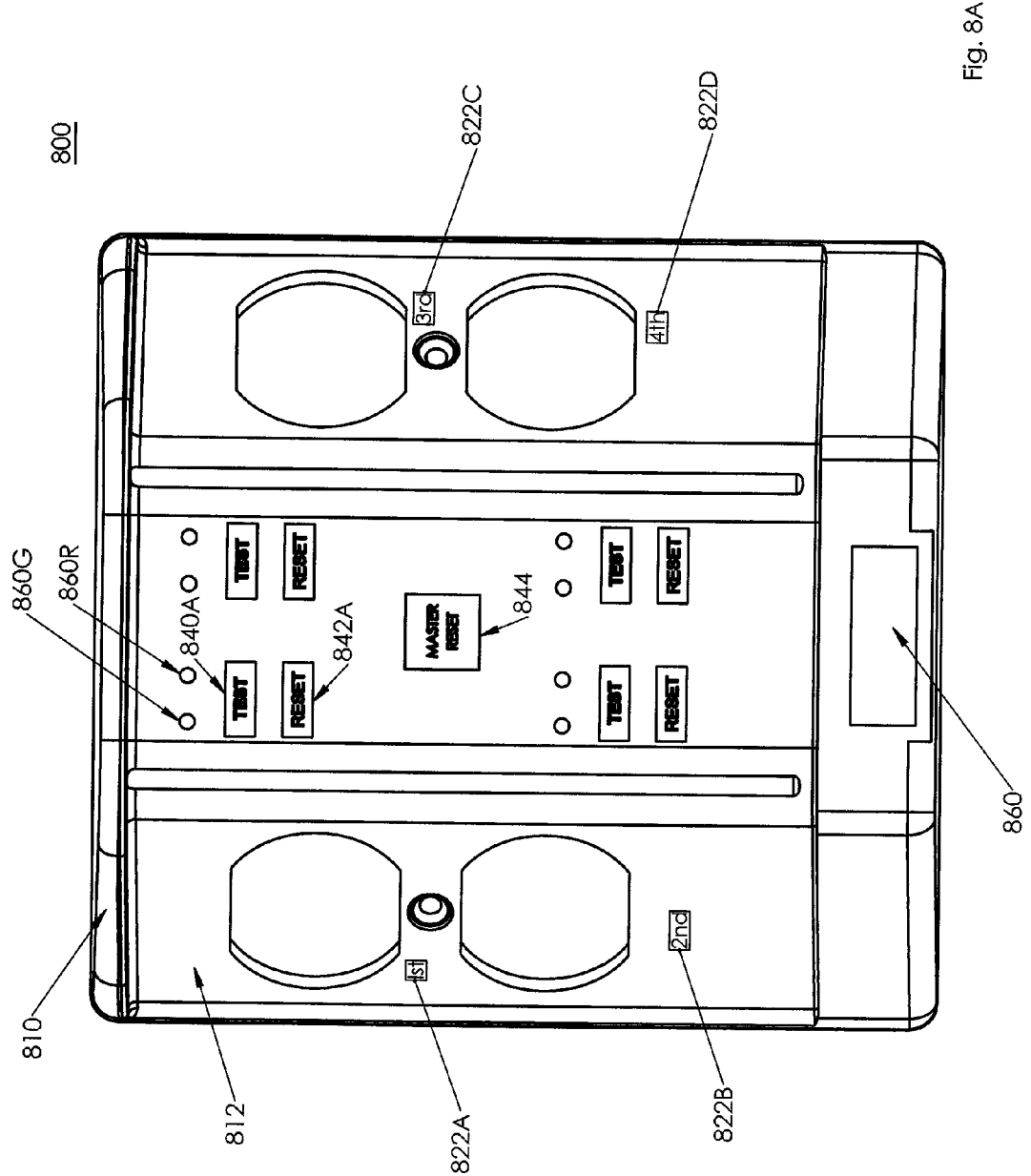
FIG. 8A shows a front view of a power supply of a third type in accordance with the second embodiment of the present invention.

FIGS. 8A-8B show a third type of power supply 800 in accordance with the second embodiment of the present invention. Overall, the housing 810 of the power supply 800 is similar to the housing 710 of power supply 700. Though the front housing 812 has a power-on indicator light 860 much like power-on indicator light 760 in front housing 712, the front housing 812 differs somewhat from front housing 712 as described below.

As seen in FIG. 8B, the circuit 870 of power supply 800 includes a plug 892 connected to ground 872, neutral 874 and line 876 leads. A pair of circuit breakers 804A, 804B are provided on two of the leads. Power supply 800 has four sockets 853A, 853B, 853C, 853D. These sockets may belong to two hospital-grade dual receptacles, not unlike dual receptacles 752A, 752B seen in power supply 700, but the 853A, 853B, 853C, 853D sockets are independently controlled. In power supply 800, the circuit 870 comprises four parallel sub-circuits, of which only one sub-circuit, sub-circuit 870A, is described, it being understood that the remaining sub-circuits are similar in construction and operation.

Sub-circuit 870A includes a test button 840A connected to a resistor 890A, and a reset button 842A for resetting the relay 888A in the power control circuit 888. A master reset button 844 is provided to reset all four sockets 853A, 853B, 853C, 853D. On the sensing side, each sub-circuit 870A comprises a current sensor 878A, a 60 Hz bandpass filter 880A, an amplifier 882A and indicator lights 860G, 860R.

The detection circuit 884 in this embodiment comprises a processor. The processor 884 works much in the same manner as processor 784, except that it receives amplified voltage signals from four amplifiers instead of just two. This results in a summed voltage that is proportional to the total patient leakage current experienced by the ground line 872. The processor 884 then compares this summed voltage with a reference voltage, such as voltage 886 that is input to the processor 884. It is understood, however, that the reference voltage may simply be a value stored in memory associated with the processor instead of being a voltage 886 input to the processor 884.

If the comparison shows that the summed voltage exceeds the reference voltage, then the processor 784 is configured to decide which of the four sockets 853A, 853B, 853C, 853D should be turned off, based on one more predetermined criteria, much the same way as in power supply 700.

In one methodology, each socket 853A, 853B, 853C 853D is assigned a priority, and the priority of each socket is indicated on the front housing 8120 by indicia 822A, 822B, 822C, 822D. In this instance, upon determining that the summed voltage exceeds the reference voltage, the processor 884 disconnects from power the lowest priority socket first, the second-lowest priority socket next, and so forth, until the summed voltage no longer exceeds the reference voltage. It should be noted, however, that the processor 884 may take into account only those sockets that are currently being used (i.e., have medical electrical equipment plugged into them and drawing current), before deciding which sockets should no longer be connected to power. This eliminates the prospect of uselessly disconnecting a socket which isn't being used anyway.

In a second methodology, the processor 884 may be configured to keep as many of the sockets 822A, 822B, 822C, 822D powered, as possible. In this instance, upon determining that the summed voltage exceeds the reference voltage, the processor 884 disconnects from power the socket having the highest patient leakage current first, the socket having the second highest patient leakage current next, and so forth, until the summed voltage no longer exceeds the reference voltage.

In a third methodology, the processor 884 may be configured to keep track of the sequence in which devices were plugged into the sockets 822A, 822B, 822C, 822D. Then, upon determining that the summed voltage exceeds the reference voltage, the processor 884 disconnects from power the socket into which a device was most recently plugged in and current drawn, then disconnects from power the socket into which a device was plugged in and current drawn second most recently, and so forth, until the summed voltage no longer exceeds the reference voltage.

Regardless of the methodology employed to select which sockets to disconnect first, the red indicator light, e.g., light 860R, may be used as a visible indicator that identified which sockets have been disconnected from power. The processor 884 may, in addition, output a signal to an audible indicator, such as a loudspeaker to serve as an additional warning.

It can thus be seen from the foregoing, that in power supply 800, the processor 884 may output a plurality of control signals so that more than one socket 853A, 853B, 853C, 853D may separately have its power disconnected.

In the above-described power supplies 100, 600, 700, 800, the rear housing was provided with a longitudinal mounting assembly, e.g., mounting assembly 130, for mounting the power supply on an IV pole. FIG. 4B shows an IV pole 490 having a built-in power supply 470 what satisfies at least one industry standard for patient leakage current. The power supply 470 is more or less permanently attached to the IV pole 490 and therefore is non-removably fixed to the IV pole, unlike power supplies 100, 600, 700 and 800 which are intended to be removably mounted to a pole 410 and thus selectively positionable anywhere therealong. The built-in power supply 470 comprises a housing on which a plurality of sockets are provided. Integrating the power supply 470 into the base of the IV pole 490 reduces the cost and weight of the whole system and further lowers the center of gravity, thus further reducing the likelihood of tipping during transport or normal use. It is understood that the circuitry of power supply 470 may comprise any of the circuitry described with respect to power supplies 100, 600, 700 and 800.

While the present invention has been described herein above in connection with a plurality of aspects and embodiments, it is understood that these aspects and embodiments were presented by way of example with no intention of limiting the invention. Accordingly, the present invention should not be limited to any specific embodiment or aspect, but rather construed in breadth and broad scope in accordance with the recitation of the claims appended hereto.

What is claimed is:

1. A pole-mountable medical electrical equipment power supply satisfying at least one industry standard for patient leakage current, and comprising:
    a housing adapted to be mounted on a pole;
    a plurality of electrical sockets suitable for receiving plugs, provided on the housing; and
    an electrical circuit comprising an isolation transformer supported by the housing, the isolation transformer connecting power from an electrical outlet to the electrical sockets, when said power supply is plugged into an electrical outlet.

2. The medical electrical equipment power supply in accordance with claim 1, further comprising:
    a channel formed on a back side of the housing and configured to receive a portion of a pole;
    a clamp assembly comprising a thumb screw supported by the housing and extending in a first direction transverse to the channel, and at least one clamping surface provided on the housing and facing in a second direction that is opposite to the first direction,
    wherein: the thumb screw and the at least one abutment surface are capable of frictionally mounting the housing to a pole, when the power supply is positioned such that a portion of a pole is received into the channel.

3. The medical electrical equipment power supply in accordance with claim 2, further comprising:
    a friction-enhancing pad formed on a wall of the channel, and configured to abut a pole, when the power supply is positioned such that a portion of a pole is received into the channel.

4. The medical electrical equipment power supply in accordance with claim 1, wherein the at least one industry standard for patient leakage current comprises a total patient leakage current that does not exceed 100 µA.

5. The medical electrical equipment power supply in accordance with claim 1, wherein the isolation transformer has a generally toroidal shape.

6. The medical electrical equipment power supply in accordance with claim 5, wherein the isolation transformer nests within a generally cylindrical cavity defined within the housing.

7. The medical electrical equipment power supply in accordance with claim 1, wherein the isolation transformer is capable of supplying a maximum current of at least 6.0 amps.

8. The medical electrical equipment power supply in accordance with claim 1, wherein:
    the electrical sockets belong to hospital grade dual receptacles; and
    a total of six electrical sockets are provided; and
    the electrical circuit further comprises at least one circuit breaker configured to protect the power supply from a power surge.

9. An intravenous (IV) pole in combination with a pole-mountable medical electrical equipment power supply satisfying at least one industry standard for patient leakage current removably mounted on a pole member of the IV pole, with at least two items of medical electrical equipment also mounted on said pole member and plugged into said power supply, wherein the pole-mountable medical electrical equipment power supply comprises:
    a housing adapted to be mounted on a pole;
    a plurality of electrical sockets suitable for receiving plugs, provided on the housing; and
    an electrical circuit comprising an isolation transformer supported by the housing, the isolation transformer connecting power from an electrical outlet to the electrical sockets, when said power supply is plugged into an electrical outlet.

10. A medical electrical equipment power supply satisfying at least one industry standard for patient leakage current, and comprising:
    a housing;
    a plurality of electrical sockets suitable for receiving plugs, provided on the housing; and
    an electrical circuit comprising:
        at least one current sensor configured to measure a patient leakage current, when the power supply is plugged into an electrical outlet and is used to power at least one item of medical electrical equipment connected to a patient;
        a detection circuit configured to determine whether the patient leakage current measured by the at least one current sensor exceeds a predetermined value based on said industry standard, and output at least one control signal in response thereto; and
        a power control circuit configured to disconnect power to at least one of said electrical sockets in response to said at least one control signal, so that the at least one industry standard for patient leakage current remains satisfied.

11. The medical electrical equipment power supply according to claim 10, wherein: the housing is adapted to be mounted on a pole.

12. The medical electrical equipment power supply according to claim 11, further comprising:
    a channel formed on a back side of the housing and configured to receive a portion of a pole;
    a clamp assembly comprising a thumb screw supported by the housing and extending in a first direction transverse to the channel, and at least one clamping surface provided on the housing and facing in a second direction that is opposite to the first direction,
    wherein: the thumb screw and the at least one abutment surface are capable of frictionally mounting the housing to a pole, when the power supply is positioned such that a portion of a pole is received into the channel.

13. The medical electrical equipment power supply in accordance with claim 12, further comprising: a friction-enhancing pad formed on a wall of the channel, and configured to abut a pole, when the power supply is positioned such that a portion of a pole is received into the channel.

14. The medical electrical equipment power supply in accordance with claim 10, wherein the at least one industry standard for patient leakage current comprises a total patient leakage current that does not exceed 100 μA.

15. The medical electrical equipment power supply in accordance with claim 10, wherein:
the electrical sockets belong to hospital grade dual receptacles;
a total of four electrical sockets are provided; and
the electrical circuit further comprises at least one circuit breaker configured to protect the power supply from a power surge.

16. The medical electrical equipment power supply in accordance with claim 10, wherein: the detection circuit comprises a comparator configured to compare a voltage signal derived from said at least one current sensor, with a reference voltage.

17. The medical electrical equipment power supply in accordance with claim 10, wherein: the detection circuit comprises a processor configured to compare a voltage signal derived from said at least one current sensor, with a reference voltage.

18. The medical electrical equipment power supply in accordance with claim 17, wherein:
the electrical circuit comprises a plurality of current sensors, each current sensor associated with at least one electrical socket; and
the processor is configured to:
sum a plurality of component voltage signals to form a summed voltage, each component voltage signal derived from one of said plurality of current sensors; and
compare said summed voltage with a reference voltage.

19. The medical electrical equipment power supply in accordance with claim 18, wherein:
the electrical circuit comprises at least four electrical sockets and four current sensors; and
the processor is further configured to: determine which of said at least four electrical sockets to disconnect from power, based at least in part on priorities assigned to each of said electrical sockets.

20. The medical electrical equipment power supply in accordance with claim 18, wherein:
the electrical circuit comprises at least four electrical sockets and four current sensors; and
the processor is further configured to: determine which of said at least four electrical sockets to disconnect from power, such that the fewest number of electrical sockets are disconnected.

21. The medical electrical equipment power supply in accordance with claim 18, wherein:
the electrical circuit comprises at least four electrical sockets and four current sensors; and
the processor is further configured to:
keep track of the sequence in which devices were plugged into the electrical sockets; and
disconnect from power the electrical socket into which a device was most recently plugged in.

22. An intravenous (IV) pole in combination with a pole-mountable medical electrical equipment power supply satisfying at least one industry standard for patient leakage current removably mounted on a pole member of the IV pole, with at least two items of medical electrical equipment also mounted on said pole member and plugged into said power supply, wherein the pole-mountable medical electrical equipment power supply comprises:
a housing adapted to be mounted on a pole;
a plurality of electrical sockets suitable for receiving plugs, provided on the housing; and
an electrical circuit comprising:
at least one current sensor configured to measure a patient leakage current, when the power supply is plugged into an electrical outlet and is used to power at least one item of medical electrical equipment connected to a patient;
a detection circuit configured to determine whether the patient leakage current measured by the at least one current sensor exceeds a predetermined value based on said industry standard, and output at least one control signal in response thereto; and
a power control circuit configured to disconnect power to at least one of said electrical sockets in response to said at least one control signal, so that the at least one industry standard for patient leakage current remains satisfied.

23. An intravenous (IV) pole in combination with a medical electrical equipment power supply non-removably fixed thereto, wherein said medical electrical equipment power supply comprises:
a housing and a plurality of electrical sockets suitable for receiving plugs provided on the housing; and
electrical circuitry configured such that the power supply satisfies at least one industry standard for patient leakage current.

24. The IV pole according claim 23, wherein said electrical circuitry comprises: an isolation transformer connecting power from an electrical outlet to the electrical sockets, when said power supply is plugged into an electrical outlet.

25. The IV pole according claim 23, wherein said electrical circuitry comprises:
at least one current sensor configured to measure a patient leakage current, when the power supply is plugged into an electrical outlet and is used to power at least one item of medical electrical equipment connected to a patient;
a detection circuit configured to determine whether the patient leakage current measured by the at least one current sensor exceeds a predetermined value based on said industry standard, and output at least one control signal in response thereto; and
a power control circuit configured to disconnect power to at least one of said electrical sockets in response to said at least one control signal, so that the at least one industry standard for patient leakage current remains satisfied.

* * * * *